United States Patent
Lee et al.

(10) Patent No.: US 8,486,898 B2
(45) Date of Patent: Jul. 16, 2013

(54) COMPOUNDS AND METHOD FOR INHIBITING THE ACTIVITY OF GELATINASE AND COLLAGENASE

(75) Inventors: Ching-Kuo Lee, Xindian (TW); Chieh-Chih Hsu, Taichung (TW); George Hsiao, Taipei (TW); Shin-Hun Juang, Taichung (TW)

(73) Assignees: Taipei Medical University (TMU), Taipei (TW); China Medical University, Taichung (TW)

( * ) Notice: Subject to any disclaimer, the term of this patent is extended or adjusted under 35 U.S.C. 154(b) by 113 days.

(21) Appl. No.: 13/167,060

(22) Filed: Jun. 23, 2011

(65) Prior Publication Data
US 2012/0022008 A1 Jan. 26, 2012

(30) Foreign Application Priority Data
Jul. 20, 2010 (TW) ................................ 99123862 A

(51) Int. Cl.
*C07H 15/18* (2006.01)
*A61K 31/7004* (2006.01)

(52) U.S. Cl.
USPC ........................................... 514/25; 536/18.2

(58) Field of Classification Search
None
See application file for complete search history.

(56) References Cited

U.S. PATENT DOCUMENTS
2003/0105031 A1* 6/2003 Rosenbloom ................... 514/27

FOREIGN PATENT DOCUMENTS
| | | |
|---|---|---|
| BR | PI 0700701 A | 9/2008 |
| JP | 10-2009-0026874 A | 3/2009 |
| JP | 2009091276 A | 4/2009 |
| JP | 2009091280 A | 4/2009 |
| JP | 2009091281 A | 4/2009 |
| KR | 10-2009-0026874 A | 3/2009 |

OTHER PUBLICATIONS
Linh, P. T. et al., Archives of Pharmacal Research, "Quantitative Determination of Salidroside and Tyrosol from the Underground Part of Rhodiola Rosea by High Performance Liquid Chromatography", 2000, vol. 23, No. 4, pp. 349-352.*
English translation of abstract of KR 10-2009-0026874 A.
Mook-Jung et al., 2002, "Neuroprotective Effects of Constituents of the Oriental Crude Drugs, Rhodiola sacra, R. sachalinensis and Tokaku-joki-to, against Beta-amyloid Toxicity, Oxidative Stress and Apoptosis", Biological and Pharmaceutical Bulletin, vol. 25, No. 8, pp. 1101-1104.
Cho et al., 2006, "Inhibitory effects of antioxidant constituents from Melothria heterophylla on matrix metalloproteinase-1 expression in UVA-irradiated human dermal fibroblasts", Journal of Cosmetic Science, vol. 57, pp. 279-289.
English translation of abstract of JP 2009091276 A, Apr. 30, 2009.
English translation of abstract of JP 2009091280 A, Apr. 30, 2009.
English translation of abstract of JP 2009091281 A, Apr. 30, 2009.
English translation of abstract of KR 10-2009-0026874 A, Mar. 16, 2009.
English translation of abstract of BR PI0700701 A, Sep. 30, 2008.

* cited by examiner

*Primary Examiner* — Layla Bland
*Assistant Examiner* — Bahar Craigo
(74) *Attorney, Agent, or Firm* — McClure, Qualey & Rodack, LLP

(57) ABSTRACT

Compounds extracted from *Rhodiola rosea* have ability to inhibit gelatinases and collagenases activity. The compounds have the chemical structure as shown below.

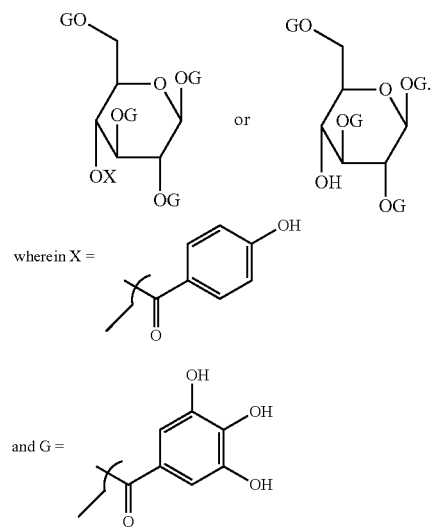

2 Claims, 5 Drawing Sheets

COMPOUNDS AND METHOD FOR INHIBITING THE ACTIVITY OF GELATINASE AND COLLAGENASE

CROSS-REFERENCE TO RELATED APPLICATION

This application claims the priority benefit of Taiwan application serial no. 099123862, filed Jul. 20, 2010, the full disclosure of which is herein incorporated by reference.

BACKGROUND

1. Technical Field

The disclosure relates to compounds and method for inhibiting the activity of gelatinase and collagenase.

2. Description of Related Art

The ageing of human skin can divide into internal and external factors in human body. Internal factors are intrinsic aging (chronological aging), which is mainly regulated by genes. External factors known as extrinsic aging or photoageing are mostly influenced by environmental stimulus (such as UV radiation, free radicals, smoking, staying up and etc). Although the mechanism in the clinical and pathological aspects of these two ageing are significant different, the increment of matrix metalloproteinase (MMPs) expression are both involved. MMPs are zinc dependent endopeptidases. MMPs are regulated by TIMPs (inhibitors of metalloproteinases), and the amount of MMPs presence equilibrium under normal condition. However, the expression of MMPs increases when expose to external stimulus, such as long-term exposure of UV irradiation, the degradation of extracellular matrix (ECM) will be performed as resulting in skin aging.

SUMMARY

Therefore, the invention herein provides compounds and a method for gelatinase and collagenase activity inhibition. The compounds with ability of gelatinase and collagenase activity inhibition are:

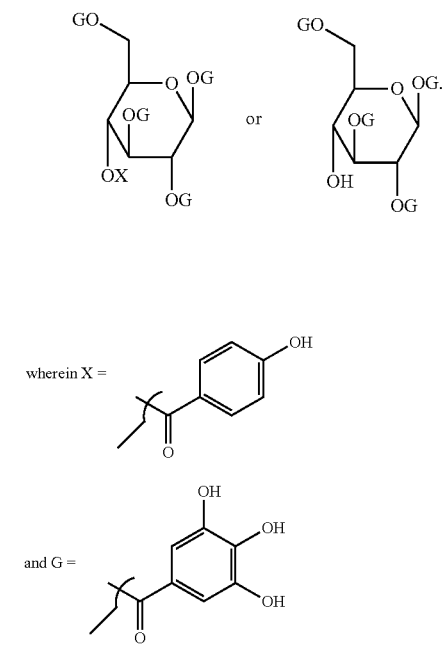

DETAILED DESCRIPTION

Figure 1:
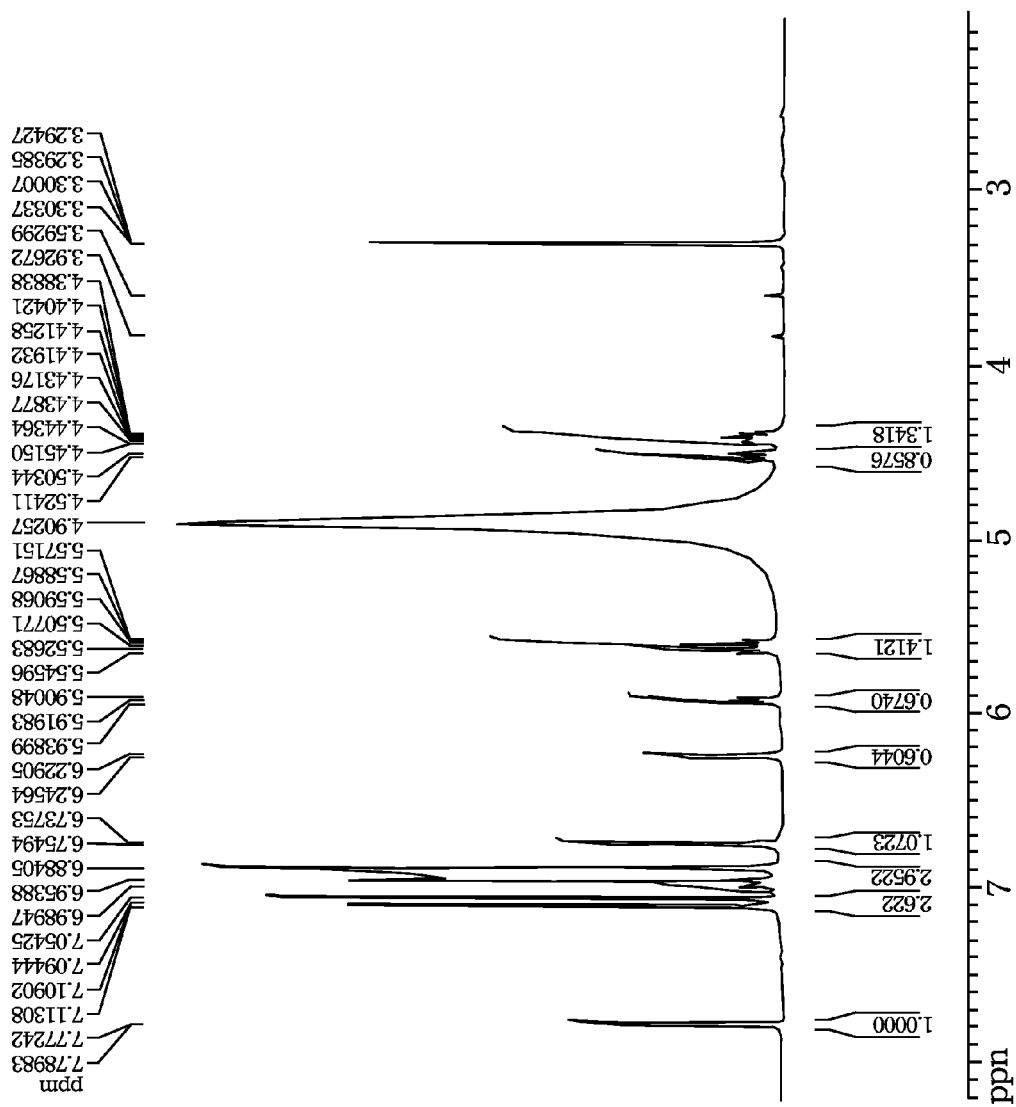
FIG. 1 is a one-dimensional $^1$H NMR spectrum of new compound 4GX.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Biological ageing is a process happened spontaneously over time, and however, it is complex in nature. The behavior of ageing can be divided into structural and functional recession. *Rhodiola rosea* is a kind of plant for anti-ageing, and thus the active skin anti-ageing ingredients in *Rhodiola rosea* must be examined.

As the mention above, matrix metalloproteinases (MMPs) are zinc-dependent endopeptidases, which including collagenase and gelatinases. Collagen can be divided into 16 types, where collagen type IV is to maintain the normal delivery of skin nutrients and moisture, and also keep skin tightening for wrinkle prevention. When skin directly exposure under UV light or during aging process, the hydrolysis of collagen type IV by collagenase increase and the biosynthesis of collagen type IV decrease, as resulting in the skin structural collapse and wrinkling.

Gelatinase includes MMP-2 (called as gelatinase A) and MMP-9 (called as gelatinase B). Gelatinase is capable of degrading proteins like non-fibronectin, fibronectin and elastin in extracellular matrix (ECM). When the skin exposure under UV light, the secretion of MMP will increase, more proteins will be destroyed by MMP and resulting in skin ageing. Collagenase and gelatinase are applied in the following experiments to test the active ingredients of *Rhodiola rosea*. Collagenase is directly used in experiments. The gelatinase is applied based on gelatinase secreting cells in experiments.

I. Preparing and Screening of *Rhodiola rosea*

Alcohol was applied to extract *Rhodiola rosea* roots to obtain the *Rhodiola rosea* alcohol extracts. The *Rhodiola rosea* alcohol extracts was first purified by partitioning with 1:1 volume of ethyl acetate and water, and then the water solution gained from the first purification was secondly purified again by butanol. After completing the previous purification processes, three parts of aqueous solutions (ethyl acetate solution, butanol solution and the water solution) were obtained from the *Rhodiola rosea* alcohol extracts.

In order to screen the desire compounds from three parts of aqueous solutions (ethyl acetate solution, the butanol solution and the water solution), screen of three aqueous solutions were taken placed, where screening method, Assay of Gelatinase and Assay of Collagenase, will be mentioned detail below. According to the results, the ethyl acetate solution was determined effective inhibition in the collagenase and gelatinase.

Afterwards, the ethyl acetate solution was purified and separated into 56 fractions by chromatography, and the fractions, effective inhibition in the collagenase and gelatinase, were selected for the further purification by Isolera™ Flash Purification System chromatography. The compositions in the *Rhodiola rosea* extract are listed bellowed on Table 1, where 4GX is a new chemical compound. And the purification processes and the chromatography are presented in order on Table 2

TABLE 1 the purified chemical compounds, 4GX and 4G, from *Rhodiola rosea*.

| Code Name | Compound name | Chemical Structure |
|---|---|---|
| 4GX | 1,2,3,6-tetra-O-galloyl-4-O-(4-hydroxybenzoyl)-β-D-glucopyranoside | 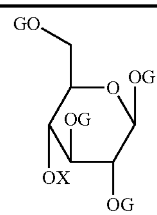 |
| 4G | 1,2,3,6-tetra-O-galloyl-β-D-glucose | 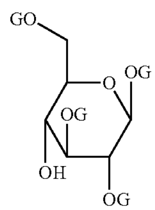 |

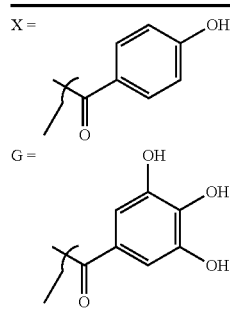

TABLE 2 the purification condition of 4GX by Isolera ™ Flash Purification System.

| Chromatography | Mobile phase (volume ratio) |
|---|---|
| 1. Normal phase chromatography | hexane:acetone = 1:4 |
| 2. Reverse phase chromatography | methanol:water = 2:1 |
| 3. Reverse phase high performance chromatography | acetonitrile:water = 1:2 |

II. The Identification of 4GX Structure

Identification of the chemical structure of the new compound 4GX was conducted. First, negative-ion mode of high-resolution electron spray ionization mass spectrometer (HRESIMS) was conducted to detect the (M-H) molecular weight of 4GX, and the resulting molecular weight of 4GX is 907.1241 and molecular formula is $C_{41}H_{32}O_{24}$.

One-dimensional proton NMR test ($^1$H-NMR), carbon 13 NMR test ($^{13}$C-NMR), and two-dimensional HMBC (Heteronuclear Multiple Bond Coherence), HMQC (Heteronuclear Multiple Quantum Coherence) and $^1$H-$^1$H COSY (Proton-Proton Correlation Spectroscopy) tests were conducted to examine 4GX by 500 MHz NMR, where deuterium solvent used herein was $CD_3OD$.

The spectrum of one-dimensional $^1$H NMR of 4GX is presented in FIG. 1, and there are 7 proton signals, $\delta_H$ 4.40 (1H, m), $\delta_H$ 4.41 (1H, m), $\delta_H$ 4.51 (1H, m), $\delta_H$ 5.58 (1H, dd, J=8.3, 9.6 Hz), $\delta_H$ 5.63 (1H, t, J=9.6 Hz), $\delta_H$ 5.92 (1H, t, J=9.6 Hz), and $\delta_H$ 6.24 (1H, d, J=8.3 Hz), in the spectrum.

Figure 2:
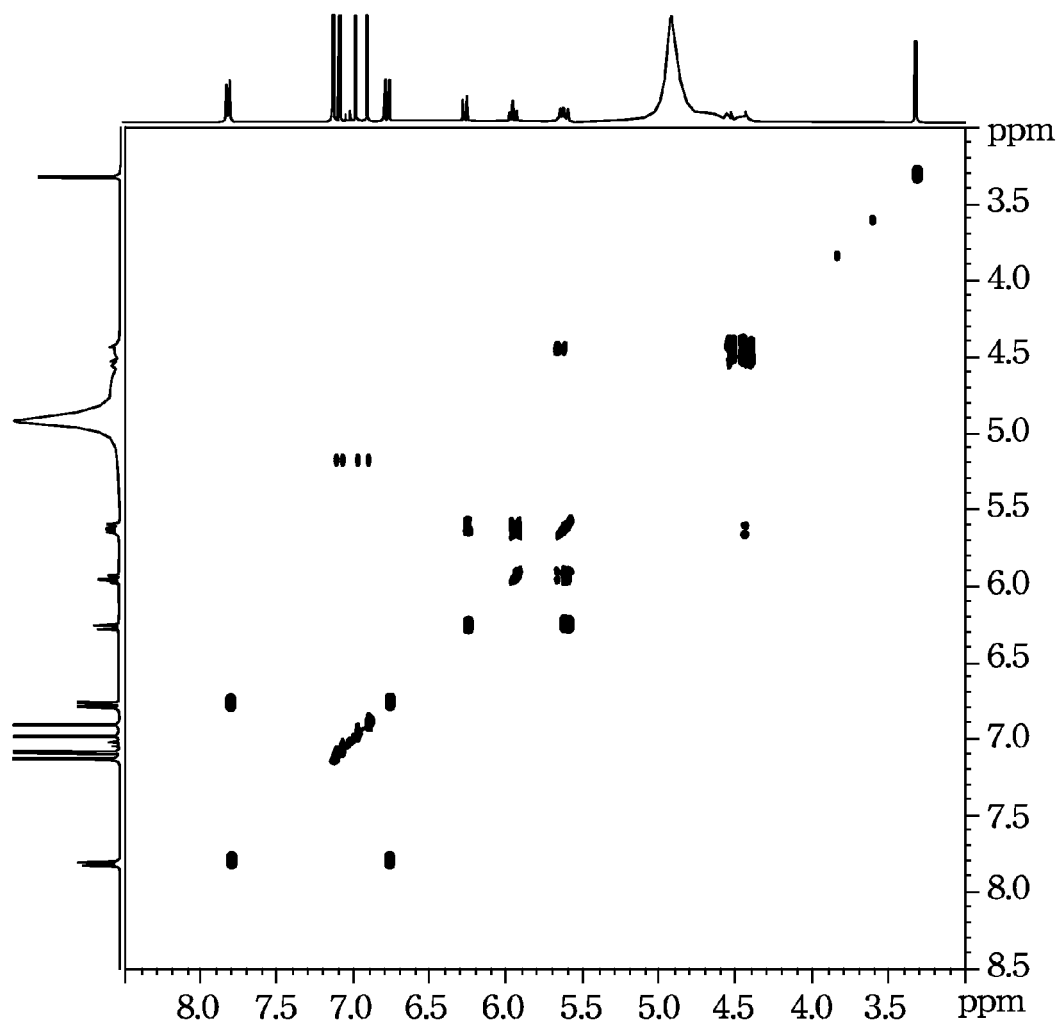
FIG. 2 is a two-dimensional $^1$H-$^1$H COSY spectrum of new compound 4GX.

The spectrum of two-dimensional $^1$H-$^1$H COSY NMR of 4GX is presented in FIG. 2. In FIG. 2, it is observed that $\delta_H$ 6.24 and $\delta_H$ 5.58 are related, $\delta_H$ 5.58 and $\delta_H$ 5.92 are related, $\delta_H$ 5.92 and $\delta_H$ 5.63 are related, $\delta_H$ 5.63 and $\delta_H$ 4.40 are related, and $\delta_H$ 4.40, $\delta_H$ 4.41 and $\delta_H$ 4.51 are related. Therefore, it is assumed that previous signals are the proton signals of β-glucopyranosyl.

Figure 3:
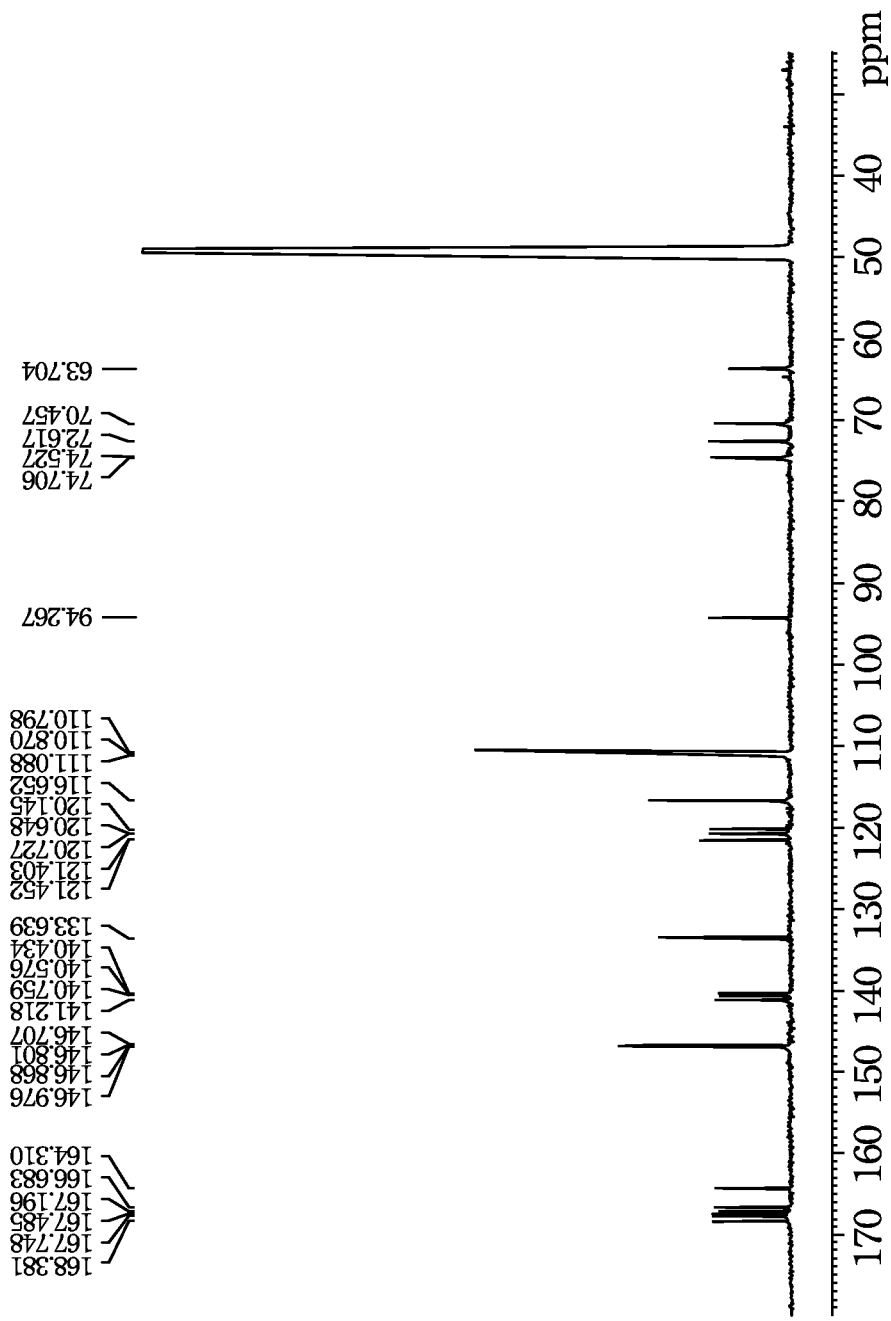
FIG. 3 is a one-dimensional $^{13}$C spectrum of new compound 4GX.
Figure 4:
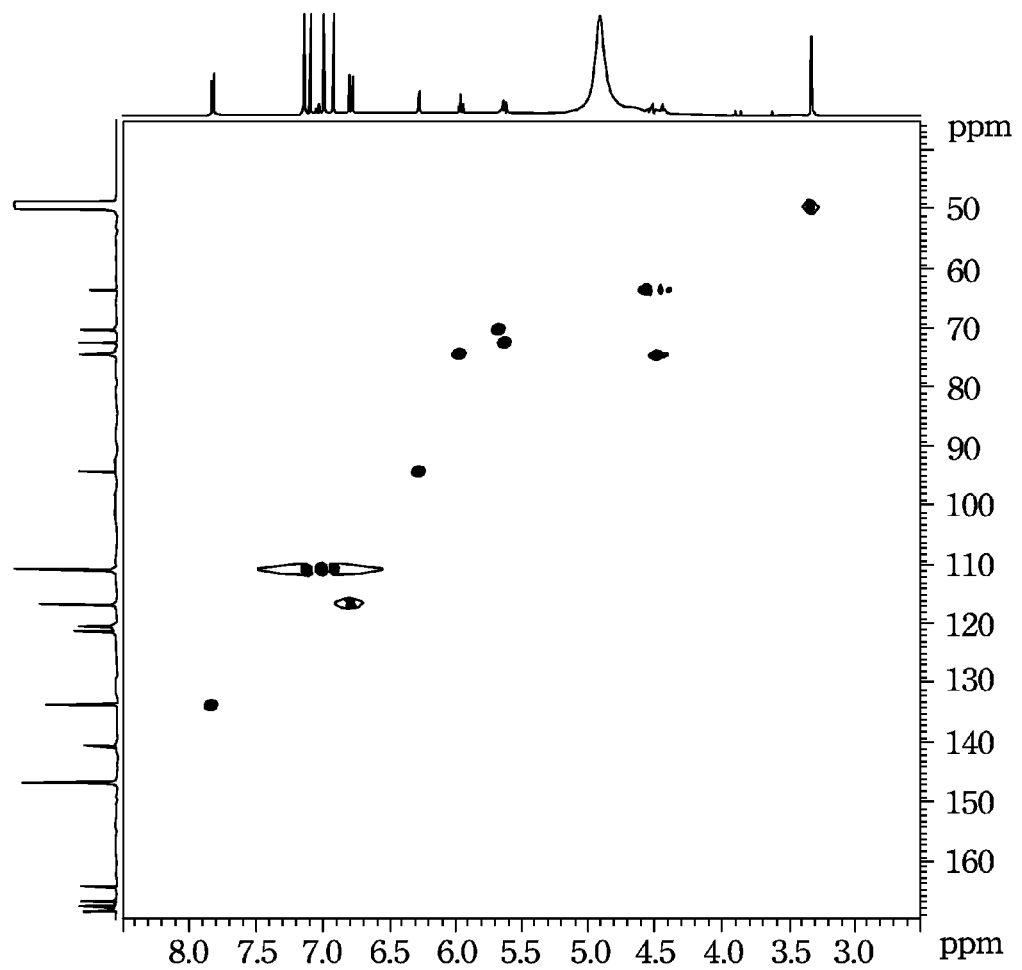
FIG. 4 is a two-dimensional HMQC spectrum of new compound 4GX.

The spectrum of one-dimensional $^{13}$C NMR of 4GX is presented in FIG. 3, and the carbon peaks of 4GX can be observed. The spectrum of two-dimensional HMQC NMR of 4GX is presented in FIG. 4. It is observed that chemical shifts ($\delta_C$) of 6 carbons (corresponding to chemical shift of the previous 7 protons) are 74.7, 63.7, 72.6, 70.5, 74.5 and 94.3, which match with the 6 carbons of β-glucopyranosyl respectively.

There are proton singlet signals $\delta_H$ 6.88, 6.95, 7.05 and 7.10 having integral value 2 respectively indicated from the one-dimensional $^1$H NMR spectrum of 4GX in FIG. 1. In addition, it is observed that the chemical shifts of two carbons are at the characteristics position of aromatic rings ($\delta_C$ 110.0-112.0) with reference to the two-dimensional HMQC NMR of 4GX in FIG. 4.

Figure 5:
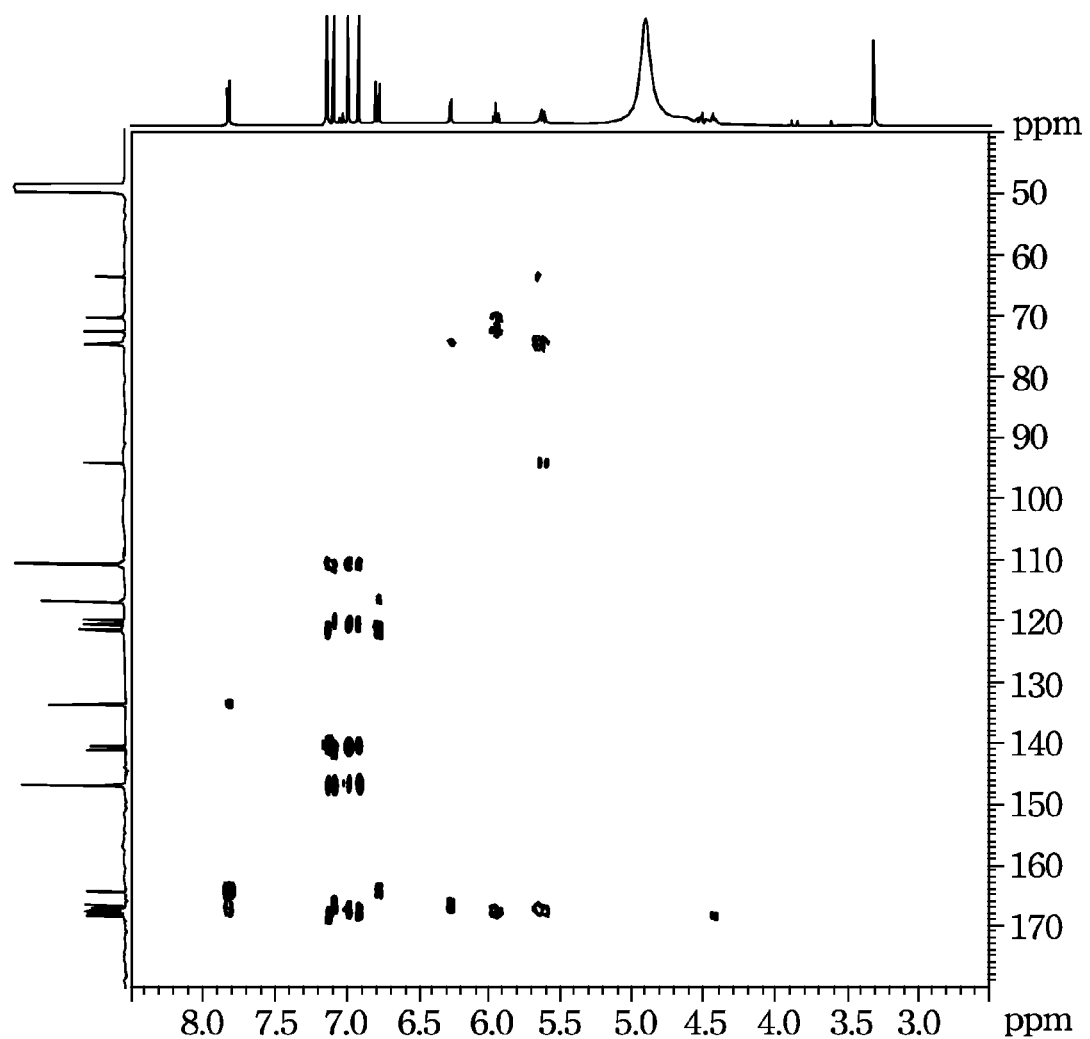
FIG. 5 is a two-dimensional HMBC spectrum of new compound 4GX.

The spectrum of two-dimensional HMBC NMR of 4GX is presented in FIG. 5, there is the carbon-hydrogen interactions over a distance of 2-3 carbon bonds. In FIG. 5, long distance coupling between aromatic hydrogen signals, $\delta_H$ 6.88, 6.95, 7.05, 7.10 of 4GX (chemical shift signals of the corresponding carbons are $\delta_C$ 110.8, 110.9, 111.1, 110.8) and $\delta_C$ 166.7, 167.5, 167.8, 168.4 (—COO—) were taken placed. Therefore, it can be determined that 4GX contains 4 sets of galloyl groups.

Besides, it is observed that $\delta_C$ 166.7 and $\delta_H$ 6.24 (Glc-1) are related, $\delta_C$ 167.5 and $\delta_H$ 5.58 (Glc-2) are related, $\delta_C$ 167.8 and $\delta_H$ 5.92 (Glc-3) are related, $\delta_C$ 168.4 and $\delta_H$ 4.41 (Glc-6) are coupling in the HMBC spectrum in FIG. 5. Since part of β-glucopyranosyl structure of 4GX and 4 sets of galloyl group are related, it is assumed that 4 sets of galloyl groups are linked to Glc-1,Glc-2,Glc-3,Glc-6 of glucose respectively according to the description above.

Moreover, $\delta_H$ 6.75 (2H, d, J=8.7 Hz) and $\delta_H$ 7.78 (2H, d, J=8.7 Hz) are doublet signals, these coupling constants are all 8.7 Hz in $^1$H NMR spectrum in FIG. 1, and therefore these two sets of proton signals belong to the substituent structures of aromatic ring in para-position. Additionally, it is confirmed that 4GX contains part of benzoic acid structure, where proton signals and $\delta_C$ 167.1 (—COO—) are related indicated from HMQC spectrum in FIG. 4 and HMBC spectrum in FIG. 5. Since —COO— ($\delta_C$ 167.1) of benzoic acid relating to $\delta_H$ 5.63 (Glc-4) are observed, it is assumed that benzoic acid substituent, X, is linked to Glc-4.

Therefore, the structure of 4GX are determined as 1, 2, 3, 6-tetra-O-galloyl-4-O-(4-hydroxybenzoyl)-β-D-glucopyranoside. The spectrum of NMR mentioning above are all presented on Table 3.

TABLE 3

NMR of 4GX.

| Glucopyran Glycosylation | $^1H$ ($\delta_H$) | $^{13}C$ ($\delta_C$) | Hydrolysis of tannin acyl group (—COO—, $\delta_C$)* | 4-hydroxyl benzoyl group (—COO—, $\delta_C$)* |
|---|---|---|---|---|
| C1 | 6.24 | 94.3 | 166.7 | |
| C2 | 5.58 | 72.6 | 167.5 | |
| C3 | 5.92 | 74.5 | 167.8 | |
| C4 | 5.63 | 70.5 | | 167.1 |
| C5 | 4.40 | 74.7 | | |
| C6 | 4.41 | 63.7 | 168.4 | |
| | 4.51 | | | |

*HMBC spectrum has cross peaks

III. Assay of Gelatinase

Incubation of HT-1080 Gelatinase Secreting Cell Line

HT-1080 cell line (ATCC:CCL-121) is a human skin fibroblasts tumor, which is a kind of adherent cell lines, secreting gelatinase, MMP-2 and MMP-9, to extracellular space.

The thawing process and primary cell culture was first accomplished. The vial containing HT-1080 cell line from liquid nitrogen was immersed immediately in water at 37° C. for one minute to thaw the cell line, then the cell line was transferred into a flask with bottom based area around 75 cm$^2$, where the flask containing medium were 15 mL of RPMI-1640 (with phenol red) (the composition of RPM I-1640 is showed in Table 4), heat-inactivated fetal bovine serum (FBS) and 1% PSQ (2 mM of 100 U/mL penicillin, 100 μg/mL streptomycin and 100 μg/mL L-glutamine), followed by incubation under 5% $CO_2$/air at 37° C. in 70% of humidity. 10% FBS was provided for cell nutrition and 1% PSQ was provided for the prevention of cross-contamination. Finally, the flask was put in the incubator.

TABLE 4 the composition of RPMI-1640 medium

| Composition | Concentration (mg/L) |
|---|---|
| Amino acid | |
| Glycine | 10 |
| L-Arginine | 200 |
| L-Asparagine | 50 |
| L-Aspartic acid | 20 |
| L-Cystine 2HCl | 65 |
| L-Glutamic Acid | 20 |
| L-Glutamine | 300 |
| L-Histidine | 15 |
| L-Hydroxyproline | 20 |
| L-Isoleucine | 50 |
| L-Leucine | 50 |
| L-Lysine hydrochloride | 40 |
| L-Methionine | 15 |
| L-Phenylalanine | 15 |
| L-Proline | 20 |
| L-Serine | 30 |
| L-Threonine | 20 |
| L-Tryptophan | 5 |
| L-Tyrosine disodium salt dihydrate | 29 |
| L-Valine | 20 |
| Vitamins | |
| Biotin | 0.2 |
| Choline chloride | 3 |
| D-Calcium pantothenate | 0.25 |
| Folic Acid | 1 |
| Niacinamide | 1 |

TABLE 4-continued the composition of RPMI-1640 medium

| Composition | Concentration (mg/L) |
|---|---|
| Para-Aminobenzoic Acid | 1 |
| Pyridoxine hydrochloride | 1 |
| Riboflavin | 0.2 |
| Thiamine hydrochloride | 1 |
| Vitamin B12 | 0.005 |
| i-Inositol | 35 |
| Inorganic salts | |
| Calcium nitrate ($Ca(NO_3)_2 \cdot 4H_2O$) | 100 |
| Magnesium Sulfate ($MgSO_4 \cdot 7H_2O$) | 48.84 |
| Potassium Chloride (KCl) | 400 |
| Sodium Chloride (NaCl) | 6000 |
| Sodium Phosphate dibasic ($Na_2HPO_4 \cdot 7H_2O$) | 800 |
| Other Components | |
| D-Glucose (Dextrose) | 2000 |
| Glutathione (reduced) | 1 |
| Phenol Red | 5 |

When the cells were saturated in the flask medium, the next subculture step must be conducted. First of all, to adopt the cell line to growth in a suspension culture, the previous medium was removed out from the flask, the monolayer surface of the cells were washed with PBS solution (phosphate buffered saline), and then the cells were incubated with 1 mL of trypsin in the same flask for 5 minute at 37° C. Afterwards, 4 ml of RPMI-1640 (with phenol red) containing 1% PSQ and 10% FBS medium was applied to inactivate the trypsin activities in the flask.

After removing the old medium, the cell suspension solution was diluted with a fresh medium. The method of replacing the fresh medium was to transfer the cell medium from the flask to the centrifugal vials, the centrifugal process was conducted at 1200 rpm at 24° C., and followed by removing the supernatant from the vials. Afterwards, the medium (RPMI-1640 (with phenol red) containing 1% PSQ and 10% FBS) was added to dilute the cell suspension solution, where the volume of the medium was four times than cell suspension solution in the vial.

Finally, a subculture process was conducted by replacing the diluted cell suspension solution with a new flask containing 10-12 ml of the previous mentioned medium. After that, repeat the cell adoption and cell suspension steps routinely when the cells are saturate on the bottom of the flask at the time interval of 2 or 3 days.

The Pre-Treatment of the Cells

Before carrying out any experimental process of HT-1080 cell lines, in order to enable HT-1080 cells to secrete more MMP-2 and MMP-9 to extracellular space, the medium RPMI-1640 containing 0.5% FBS (without phenol red) was applied when conducting the subcultivation process. After centrifugation, the medium RPMI-1640 containing only 0.5% FBS was added into centrifugal vials to resuspend the cells, and 20 μL of cell suspension solution was transferred into eppendorfs to mixed with 20 μL Trypan blue for cell dyeing. Finally, calculation of the cell concentration was accomplished by using hemocytometer through optical microscope.

Suitable amount of the medium RPMI-1640 (based on the cell concentration obtained previous) containing only 0.5% FBS (without phenol red) was applied into the remaining the cell suspension solution, as the resulting concentration of the cell suspension solution around 5×10$^5$ cells/mL. Afterwards, 500 μL of cell suspension solutions was transferred onto 24-well cell culture plates, followed by 24 hours incubation at 37° C. for the further experiments.

MTT Cell Viability Assay

To test the cytotoxicity of 4GX and 4G to HT-1080 cell lines, the cell viability assay need to be conducted. MTT cell viability assay was chosen for this experiment.

The principle of a cell viability assay is the conversion of a yellow tetrazolium salt (MTT; 3-(4,5-Dimethylthiazol-2-yl)-2,5-diphenyl tetrazolium bromide) into a purple product formazan via lactate dehydrogenase in intact mitochondria, where formazan can be dissolved in dimethylsulfoxide (DMSO). Thus, the increasing yield of resulting product formazan stands for increasing the percentage of cell vitality.

The cell suspension solution (with concentration about $5 \times 10^5$ cells/mL) of the previous cell pre-treatment process was placed to a 24-well cell culture plates with 24 hours of incubation under 5% of $CO_2$/air at 37° C. in 70% of humidity, in order to allow cells to grow adherent on the well. After 24 hours of incubation, 1 μL of the solutions containing chemical compounds, 4GX and 4G, prepared in different concentrations (5-100 μM) were applied into each well respectively as vehicle controls, whereas the well applied without any chemical compounds as blank. Finally, the 24-well cell culture plate was placed in incubator for 22 hours of incubation.

Subsequently, the following steps need to avoid the light. After 22 hours of incubation, 50 μL of 5.5 mg/mL MTT was applied in each well for 2 hours of incubation at 37° C. Afterwards, the supernatant was removed from 24-well cell culture plates, and 400 μL DMSO was applied to dissolve the purple product formazan for 15 minutes by shaker at 50 rpm. 150-200 μL of the solution were taken out from each well to examine the adsorption value by ELISA at wavelength 550 nm.

The formula for calculation of cell vitality is presented following:

(Adsorption value of vehicle control/blank)×100%

The results of the cell survival test are showed in Table 5, where the results are presented in mean±S.E.M. (standard error of the mean) in Table 5.

According to the results presented in Table 5, the cell vitalities are all above 85% for both 4GX and 4G with concentration to 100 μM, and thus it is believed that 4GX and 4G are non-cytotoxicity.

Gelatin Zymography

To evaluation the inhibitory effectiveness of gelatinase of 4GX and 4G, a gelatin zymography is needed to be conducted.

The cell suspension solution (with concentration about $5 \times 10^5$ cells/mL) of the previous cell pre-treatment process was placed to a 24-well cell culture plates for 24 hours of incubation at 37° C. Subsequently, 1 μL of the solutions, containing 4GX and 4G, in different concentrations from 10 to 100 μM (10, 20, 50, 100 μM) were applied into each well respectively as vehicle controls, 1 μL of catechin in concentration of 100 μM was applied into the well as a positive control, whereas the well applied without any compounds is as blank, followed by 24 hours of incubation at 37° C. Afterwards, the plate was placed into ice to terminate the reaction, the supernatant of each well were taken out separately for the further experiments.

Supernatants and two volume of a sample loading dye (500 mM Tris-HCL, 25% Glycerol, 10% SDS, 0.32% Bromophenol blue, pH 6.8) and one volume of a dye were mixed together to use as the indicator of running end point. Afterwards, the enzyme activity was analyzed by polyacrylamide gel electrophoresis (PAGE).

1% of gelatin and 10% of polyacrylamide were contained in the gel of PAGE, where gelatin acts as the substrate for gelatinase (pro MMP-2, MMP-2 and pro MMP-9). The running buffer was 25 mM Tris-base, 192 mM Glycerol and 0.1% sodium dodecyl sulfate (SDS), pH 8.3, and the power supply was 125 V/80 mA.

Following the electrophoresis, the gel was washed with 2.5% Triton X-100 at 24° C. twice in 30 minutes to remove the dye and SDS from the gel. Afterwards, the gel was incubated with a reacting buffer (50 mM Tris-base, 200 mM NaCl, 5 mM $CaCl_2$ and 0.02% Brij 35, pH 7.5) at 37° C. for 24 hours in a thermostatic cabinet, enabling gelatinase enzymatically react with gelatin. The fixing solution (7% acetic acid and

TABLE 5 the results of cell viability test of MTT assay

| | Blank* | 4G | | | |
| --- | --- | --- | --- | --- | --- |
| | | 10 μM | 20 μM | 50 μM | 100 μM |
| Vitality (%) | 100 | 93.45 ± 4.91 | 87.30 ± 1.93 | 93.06 ± 4.41 | 87.81 ± 7.83 |
| | Vehicle controls** | 4GX | | | |
| | | 10 μM | 20 μM | 50 μM | 100 μM |
| Vitality (%) | 100.90 ± 4.05 | 97.18 ± 6.52 | 100.78 ± 4.06 | 105.48 ± 2.18 | 94.31 ± 9.76 |

*Blank, setting blank as 100.
**Vehicle controls, are presented to demonstrate the cell vitalities are not affected by DMSO Generally, it is believed that the test substance is substantially non-cytotoxicity when the resulting cell vitalities are more than 80% or 85% after exposing the cells in an effective concentration of test substance during the survival test.

40% methanol) was subsequently applied to the gel for 30 minutes, in order to secure the proteins onto the gel. After 30 minutes, the gel was stained with Brilliant Blue G-Colloidial, and then destained with the destain solution (10% acetic acid and 40% methanol) for visualization of the gelatinase reactive positions against the background of the gel.

Finally, the gel was then analyzed by image analysis system (Vilber Lounmat, France), and the analysis software was Bio-1 Dversion 99. Setting the blank as reference, setting as 1, and the other groups are presented in relative values in contrast to blank.

The formula for calculating the inhibitory effectiveness is presented below. The results of gelatin zymography are provided on Table 6, and all values are presented as Mean±S.E.M.

(the values of blank−vehicle controls)×100%

TABLE 6 the inhibitory effectiveness of 4GX and 4G to gelatinase

| Inhibitory effective- ness (%) | 4GX | | | 4G | | |
|---|---|---|---|---|---|---|
| | Pro MMP-2 | MMP-2 | pro MMP-9 | Pro MMP-2 | MMP-2 | pro MMP-9 |
| 10 μM | 15.83 ± 4.48 | 25.46 ± 11.50 | 3.80 ± 4.8 | 10.13 ± 5.85 | 29.93 ± 5.99 | 18.73 ± 8.86 |
| 20 μM | 31.53 ± 9.79 | 63.57 ± 4.35 | 15.83 ± 4.48 | 16.80 ± 1.71 | 48.07 ± 3.63 | 28.70 ± 12.54 |
| 50 μM | 62.30 ± 2.43 | 76.20 ± 6.88 | 32.17 ± 2.77 | 30.13 ± 2.20 | 73.27 ± 7.31 | 44.13 ± 11.32 |
| 100 μM | 82.01 ± 3.08 | 85.07 ± 3.78 | 45.47 ± 3.57 | 39.40 ± 6.78 | 80.47 ± 2.19 | 53.50 ± 13.25 |
| Positive controls (P) (100 μM) | 56.30 ± 9.89 | 86.77 ± 11.34 | 64.30 ± 32.57 | 72.97 ± 9.76 | 85.00 ± 5.50 | 76.07 ± 3.76 |
| $IC_{50}$ (μM) | 30.00 ± 6.06 | 16.27 ± 1.63 | >100 | 99.63 ± 0.18 | 23.01 ± 4.86 | >100 |

* $IC_{50}$, half maximal inhibitory concentration)
* Positive controls (P), 100 μM of catechin was applied.

Generally, it is believed that the substance has substantially inhibitory effectiveness when the resulting values of inhibitory effectiveness (%) of the substance are larger than the positive controls. According to the results from Table 6, it indicates that the inhibition activities of 4GX or 4G to MMP-2 are both desirable. The results are comparable with positive controls (100 μM catechin) when 4GX and 4G in the concentration of 100 μM were applied. Besides, the inhibitory activity of the 100 μM 4GX to ProMMP-2 even superior to the results of positive controls (100 μM catechin).

IV. Assay of Collagenase

Collagenase type IV and DQ-gelatin was applied in this experiment, where $DQ^{198}$ (EnzChek Gelatinase/Collagenase Assay Kit, E-12055) is a kind of fluorescent material, which can bonded with gelatin to form DQ-gelatin. Since the capability of gelatin hydrolysis of collagenase type IV has been demonstrated, DQ™-gelatin can be a substrate for collagenase. Thus, the principle of this experiment is that the activity of collagenase is examined by measuring emission intensity of DQ fluorescent as that the chemical bonding between DQ-gelatin can be enzymatically digested by collagenase.

The fluorescence intensity can be measured in a florescence micro-plate reader equipped with standard fluoresce in filters. Digested product from the DQ-gelatin and DQ collagen substrate has absorption wavelength at 495 nm and fluorescence emission wavelength at 515 nm. Therefore, the activity of collagenase can be determined when the fluorescence emission intensity at 515 nm larger than the blank. In other word, the resulting fluorescence emission intensity would decrease at 515 nm if the collagenase inhibitors were applied. The results of collagenase assay are provided on Table 7, and all values are present as Mean±S.E.M.

TABLE 7 the result of collagenase assay

| | 4G | | 4GX | | Positive controls (P) | |
|---|---|---|---|---|---|---|
| Samples | 20 μM | 40 μM | 20 μM | 40 μM | 20 μM | 40 μM |
| Inhibitory effectiveness % | 52.12 ± 4.30 | 61.73 ± 1.98 | 23.51 ± 2.81 | 47.50 ± 2.90 | 12.80 ± 5.40 | 38.41 ± 1.43 |

*p, positive controls, 1, 10-phenanthroline were applied.

The inhibitory effectiveness of 4G and 4GX are obvious better than positive controls, and 50% of the inhibitory effectiveness are achieved when 20 μM of 4G were applied according to Table 7. Since 4G and 4GX are able to decrease the activities of collagenase, the prevention of ageing can be achieved by 4G and 4GX.

V. Transdermal Penetration Test

To evaluation the effectiveness of topical use of 4G and 4GX, the transdermal penetration test of 4G was performed.

Franz-type diffusion cell is the apparatus for this experiment, where its structure as a set of vertical double-diffusion and detachable glass containers. The upper donor chamber is a hollow cylindrical for the sample injection, and the bottom of the upper donor chamber has a contacting surface. The lower receptor chamber is double-layered hollow cylindrical diffusion container, where the inner layer of the receptor chamber made of glass contains a fluid for sampling, the outer layer of the receptor chamber is filled with circulating water kept at 37±1° C. for the human body simulation. The contact area between the donor chamber and the receptor chamber is 0.785 $cm^2$ (the actual penetration area), and the intermediate is fixed with nude and white mice (all three) skins (epidermis facing upwards) by metal clips as the in vitro transdermal penetration barriers.

The experimental method is presented below. First, 4G was dissolved in 30 wt % propylene glycol aqueous solution, followed transferring 0.5 mL of the aqueous solution (containing 0.25 mg) of 4G into the donor chamber of the Franz-type diffusion cell, and top of the open-ended donor chamber was covered with Parafilm® tightly, and the inner receptor chamber was filled with 5.5 mL of the buffer solution (30 wt % ethanol, phosphate buffer solution, pH 7.4), with continuously stirring at 600 rpm. 0.3 mL of the buffer solution was respectively sampled at time points of 1, 2, 4, 6, 8, 10, 12, 24, 36, and 48 hours, and with complete replacement of 0.3 mL of the buffer solution to keep fluid in the diffusion cell the same volume. Finally, the final compound of 4G accumulated in the fluid of the receptor chamber, was analyzed by liquid chromatography tandem mass spectrometry (LC-MS) to investigate the amount of the 4G penetrating through skins and reaching to the blood vessel, After completing the previous experimental step, the compound, 4G, on the surface of nude and white mice skin were washed with deionized water. Afterwards, the skins were trimmed into the circles with diameter equal to the donor chamber, and following record the skin weight. The skins then placed in homogenizer with 1 mL alcohol at speed 300 rpm for 5 minutes, and followed with centrifugation process at 10000 rpm for 5 minutes. The supernatant was filtered by 0.45 μm PVDF and quantified the content of 4G by LC-MS.

The accumulated amounts of 4G of the fluid were nearly zero in the receptor chamber, the amount of 4G in mice skins are presented on Table 8.

TABLE 8

| | the amount of 4G in the mince skins | | |
|---|---|---|---|
| Samples | The amount of 4G in the skins (μg) | Average (μg) | Percentage of 4G in the mouse skins |
| Nude mice | 1  1.42 | 1.17 ± 0.21 | 27.84% |
| | 2  1.02 | | |
| | 3  1.09 | | |
| White mice | 4  8.82 | 6.07 ± 2.43 | 74.84% |
| | 5  4.23 | | |
| | 6  5.16 | | |

It is observed that 4GX and 4G are capable of inhibiting gelatinase and collagenase according to the embodiment disclosed herein. Besides, 4GX and 4G can penetrate epidermal layer to basal layer and dermal layer of skin to inhibit the activity of gelatinase and collagenase, and thus mitigation of skin ageing can be achieved.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. A purified compound 4GX having a chemical formula as follow:

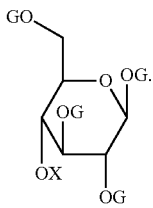

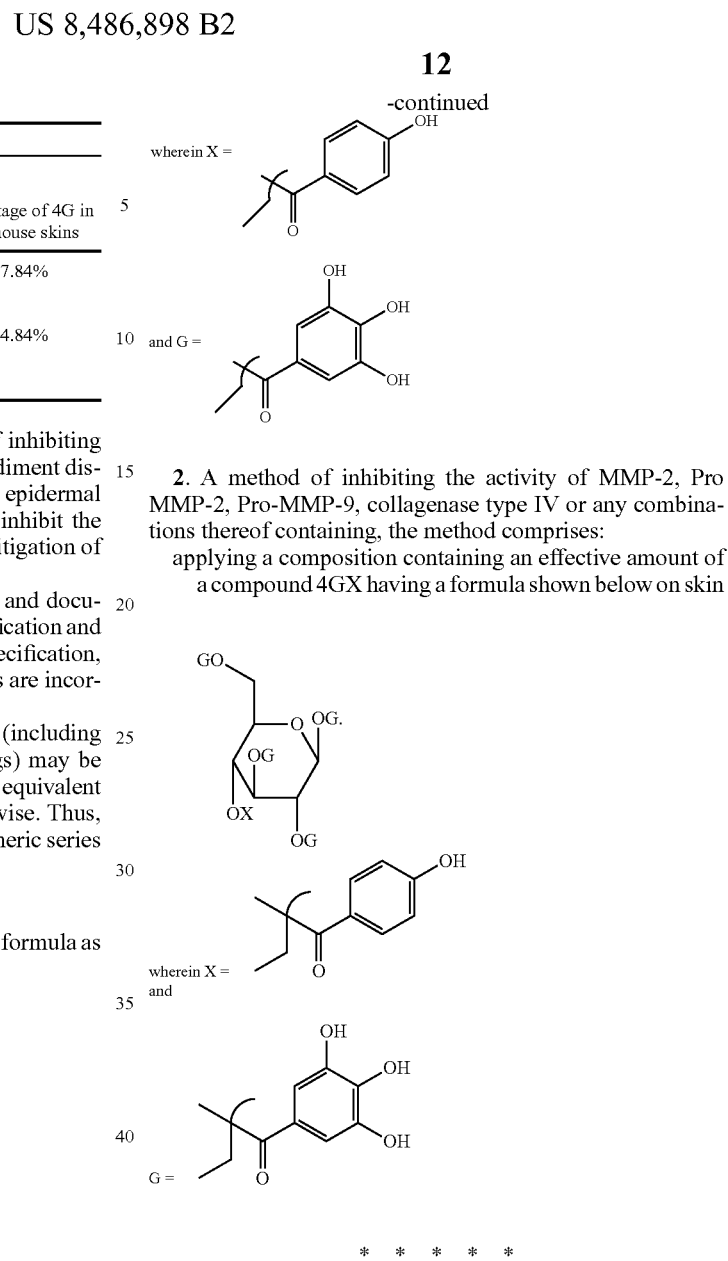

2. A method of inhibiting the activity of MMP-2, Pro MMP-2, Pro-MMP-9, collagenase type IV or any combinations thereof containing, the method comprises:
applying a composition containing an effective amount of a compound 4GX having a formula shown below on skin

* * * * *